United States Patent
Vila Pahi et al.

(10) Patent No.: US 6,680,304 B2
(45) Date of Patent: Jan. 20, 2004

(54) DISACCHARIDES WITH ANTI-ARTHROSIC PROPERTIES

(75) Inventors: Francisco Javier Vila Pahi, Barcelona (ES); Francesc Flores Salgado, Mataro (ES); Ramon Ruhi Roura, Barcelona (ES); Narcís Arnau Pastor, Girona (ES)

(73) Assignee: Bioiberica, S.A., Palafolls (ES)

( * ) Notice: Subject to any disclaimer, the term of this patent is extended or adjusted under 35 U.S.C. 154(b) by 0 days.

(21) Appl. No.: 10/332,505
(22) PCT Filed: Jul. 5, 2001
(86) PCT No.: PCT/ES01/00265
§ 371 (c)(1), (2), (4) Date: Jan. 10, 2003
(87) PCT Pub. No.: WO02/08239
PCT Pub. Date: Jan. 31, 2002

(65) Prior Publication Data
US 2003/0181400 A1 Sep. 25, 2003

(30) Foreign Application Priority Data
Jul. 13, 2000 (ES) .......................... P200001741

(51) Int. Cl.⁷ ................. A61K 31/7016; A61K 31/715; C07H 3/04; C07H 5/06
(52) U.S. Cl. ..................... 514/53; 514/25; 514/825; 514/886; 536/4.1; 536/21; 536/115; 536/118; 536/124
(58) Field of Search .................. 514/53, 825, 886, 514/25; 536/4.1, 21, 115, 124, 118

(56) References Cited

U.S. PATENT DOCUMENTS 4,761,401 A * 8/1988 Couchman et al.

FOREIGN PATENT DOCUMENTS

| EP | 0211610 | 2/1987 |
| EP | 704216 | 4/1996 |
| WO | WO 9309766 | 5/1993 |
| WO | WO 00/47163 | 8/2000 |
| WO | WO 0061592 | 10/2000 |

OTHER PUBLICATIONS

Jacquinet et al, *Carbohydrate Research*, 314(3–4): 283–288 (1998).
Jacquinet et al, *Carbohydrate Research*, 199(2):153–181 (1990).
Takanashi et al, *J. Amer. Chem. Soc.*, 84:3029 (1962).
Geciova et al, *Macromol. Chem. Phys.*, 196:2891–2903 (1995).

* cited by examiner

*Primary Examiner*—Samuel Barts
*Assistant Examiner*—Michael C. Henry
(74) *Attorney, Agent, or Firm*—Sughrue Mion, PLLC

(57) ABSTRACT

The invention relates to novel disaccharides of formula (I), wherein $R^1$ is selected from the group consisting of hydrogen, linear or branched ($C_1$–$C_4$) alkyl, phenylalkyl with less than ten carbon atoms and —$COCH_3$; $R^2$ is selected from the group consisting of hydrogen, —$COCH_3$ and $SO_3M$; $R^3$ is selected from the group consisting of hydrogen, linear or branched ($C_1$–$C_4$) alkyl, phenylalkyl with less than ten carbon atoms, —$COCH_3$ and y —COPh, Ph being phenyl; G is selected from amongst —$COOR^4$ and —COOM, $R^4$ is selected from the group consisting of hydrogen, ($C_1$–$C_2$)-alkyl and arylalkyl with less than sixteen carbon atom; A is selected from the group consisting of hydrogen, —$SO_3H$, —$SO_3M$ and —$COCH_3$; B is selected from the group consisting of hydrogen, —$SO_3H$, —$SO_3M$ and —$COCH_3$, wherein either A or B are necessarily either —$SO_3H$ or —$SO_3M$, M being a an organic or metallic cation. Said compounds can be used as anti-arthritic agents, anti-inflammatory agents or to control blood coagulation.

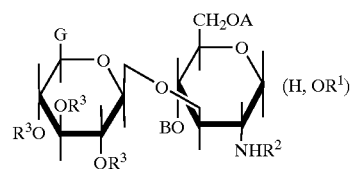

(I)

15 Claims, No Drawings

DISACCHARIDES WITH ANTI-ARTHROSIC PROPERTIES

CROSS-REFERENCE TO RELATED APPLICATION

This Application is a 371 of PCT/ES01/00265, filed Jul. 5, 2001. The disclosure of which is incorporated herein by reference in its entirety.

The present invention relates to novel disaccharides, the solvates and pharmaceutically acceptable salts thereof, and to the pharmaceutical compositions containing them. This invention also refers to a process for preparing the novel disaccharides, as well as to the therapeutical use thereof.

STATE OF THE ART IN RELATION TO THE INVENTION

Arthrosis (osteoarthritis) is the most common articular rheumatic disease, affecting most people over 65 years of age, characterised by a gradual degradation of the cartilaginous tissue, together with the presence of inflammation and pain. The term arthrosis describes a disease in which the hyaline cartilage of the articulations is destroyed.

At present, therapy is centred on relieving the symptoms, since no agent has yet been found that provides a proven reduction of the progression of the damage to the cartilage, although there is some clinical evidence for chondroitin sulphate and hyaluronic acid.

The substances that act on the symptoms include: rapid action substances such as analgesics, non steroidal anti-inflammatory drugs (NSAIDS) and corticoids, and substances that have a somewhat slower effect, known as SYSADOA (Symptomatic slow acting drug for osteoarthritis) (M. G. Lequesne, Rev. Rhum. (Eng./Ed.), 61, 69–73 (1994)), which include hyaluronic acid, chondroitin sulphate and glucosamine sulphate.

Symptomatic slow acting drugs have the additional advantage that they are safer than NSAIDS (E. Maheu, European Journal of Rheumatology and Inflammation, 15, 17–24 (1995)), and have longer-lasting effects, which even persist for some months after the cessation of treatment.

Recently, clinical trials conducted with hyaluronic acid (V. Listrat et al., Osteoarthritis Cart., 5, 153–160 (1997)) and with chondroitin sulphate (G. Verbruggen et al., Osteoarthritis Cart., 6 (Supplement A), 37–38 (1998)) have for the first time provided evidence of the possibility that these two compounds, besides acting as SYSADOA, may influence and delay the course of the arthrosic disease, (chondro-protective agents).

Hyaluronic acid is a non-sulphate glycosaminoglycan of natural origin, with a polymeric structure composed of disaccharides of N-acetylglucosamine and glucuronic acid.

Hyaluronic acid is extracted from mammal organs and/or tissues. One known problem lies in the fact that, depending on how it is obtained, the molecular weight of the product can vary, which, together with the fact that it may come from different sources, means that there are several hyaluronic acids that may or may not have the same clinical effects.

The disaccharides of the present invention are structurally related to the dimers present in the polymeric structure of hyaluronic acid, in as much as they are disaccharides with β-(1→3) unions between the glucuronic acid and the glucosamine, but the disaccharides of the present invention always contain a sulphate group in the C-4 and/or the C-6 of the glucosamine ring.

Some compounds have been described in the bibliography that can also be considered to be structurally related to the compounds of the present invention.

J. R. Couchman et al. (EP 211610) disclose esterified disaccharides that differ from the compounds of the present invention in the nature of the alkyl root of the ester group (—COOR'). These compounds also differ from those of the present invention in that they are useful for stimulating hair growth and for the treatment of baldness.

The disaccharides that are repeated in the structure of chondroitin sulphate, the sulphated derivative both in position 4 and position 6 of the N-acetylgalactosamine, are commercially available, and they are obtained by degradation of the natural polymers or by chemical synthesis (J. C. Jacquinet, Carbohydrate Research, 199, 153–181 (1990); J. C. Jacquinet et al. Carbohydrate Research, 314, 283–288 (1998)), but they differ from the compounds of the present invention in that they contain galactosamine instead of glucosamine. The biological activities of these disaccharides have not been described to date.

Hartung et al. (WO 9309766) disclose a method for treating human and horse painful arthopathic conditions, administering parenterally, intramuscularly, or transdermally an effective amount of a composition containing at least one chondroitin sulfate salt. In the same manner, Nocelli et al. (EP 704216) disclose a gel-like pharmaceutical composition containing chondroitin sulfate salts for the treatment of arthrosis by means of an oral administration. The chondroitin derivatives described by Hartung et al. and Nocelli et al. differ from the compounds of the present invention in that they refer to a polymeric structure and that they contain a galactosamine moiety instead of a glucosamine.

Therefore, it is evident that the obtention of new compounds for the treatment of arthrosis and its symptoms, such as inflammation and pain, is still a problem in therapy.

DISCLOSURE OF THE INVENTION

The present invention provides new disaccharides of formula (I),

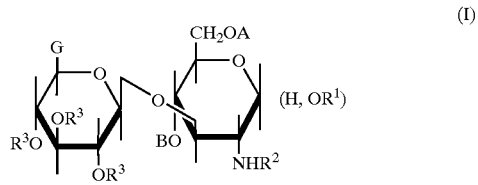

in which:
$R^1$ is-selected from the group consisting of: hydrogen, linear or branched ($C_1$–$C_4$)-alkyl, phenylalkyl of less than ten carbon atoms and —$COCH_3$;

$R^2$ is selected from the group consisting of: hydrogen, —$COCH_3$ and $SO_3M$;

$R^3$ is selected from the group consisting of: hydrogen, linear or branched ($C_1$–$C_4$)-alkyl, phenylalkyl of less than ten carbon atoms, —$COCH_3$ and —COPh, where Ph is phenyl;

G is selected from between —$COOR^4$ and —COOM, where $R^4$ is selected from the group consisting of: hydrogen, ($C_1$–$C_2$)-alkyl and arylalkyl of less than sixteen carbon atoms;

A is selected from the group consisting of: hydrogen, —$SO_3H$, —$SO_3M$ and —$COCH_3$; and B is selected from the group consisting of: hydrogen, —$SO_3H$, —$SO_3M$, and —$COCH_3$, where either A or B is necessarily either —$SO_3H$, or —$SO_3M$, and where M is an organic or metallic cation.

The invention also includes the solvates and the pharmaceutically acceptable salts of the compounds of formula (I):

The compounds of formula (I) have an anomeric carbon in their structure. This invention includes anomeric forms α and β, and their mixtures.

In a preferred embodiment, the compounds of formula (i) are those where: G is —COOR$^4$, or —COOM, where R$^4$ is ($C_1$–$C_2$)-alkyl, or arylalkyl of less than sixteen carbon atoms, and M is a metallic cation.

More preferred are the compounds of formula (I) where: R$^1$ is hydrogen, R$^2$ is —COCH$_3$ and R$^3$ is hydrogen. Equally preferred are the compounds of formula (I) where: R$^1$ is methyl, R$^2$ is —COCH$_3$ and R$^3$ is hydrogen.

Even more preferred are the compounds of formula (I) where A is hydrogen and B is —SO$_3$M, or where A is —SO$_3$M and B is hydrogen, or where A and B are —SO$_3$M, and M is a metallic cation.

Especially preferred are the compounds of formula (I) where: M is the sodium cation.

Particularly especially preferred embodiments of this invention are those in which the compounds of formula (I) are one of the following:

methyl 2-acetamido-2-deoxy-3-O-(β-D-glucopyranosyluronic acid)-6-O-sulfo-α-D-glucopyranoside, disodium salt;

methyl 2-acetamido-2-deoxy-3-O-(β-D-glucopyranosyluronic acid)4-O-sulfo-α-D-glucopyranoside, disodium salt;

methyl 2-acetamido-2-deoxy-3-O-(β-D-glucopyranosyluronic acid)4,0-di-O-sulfo-α-D-glucopyranoside, trisodium salt;

2-acetamido-2-deoxy-3-O-(β-D-glucopyranosyluronic acid)-6-O-sulfo-D-glucopyranose, disodium salt;

2-acetamido-2-deoxy-3-O-(β-D-glucopyranosyluronic acid)4-O-sulfo-D-glucopyranose, disodium salt;

2-acetamido-2-deoxy-3-O-(β-D-glucopyranosyluronic acid)4,6-di-O-sulfo-D-glucopyranose, trisodium salt.

Another embodiment of this invention is a process for preparing a compound of formula (I).

According to this invention, compounds of general formula (I) are obtained by a process characterised in that a monosaccharide of formula (II),

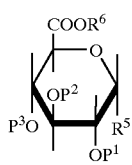

(II)

where R$^5$ represents a reactive group that can establish a β-(1→3) union with the free hydroxyl in the monosaccharide of formula (III), R$^6$ can be equivalent to group R$^4$ in (I) or a group that protects carboxyl groups that can be eliminated later, P$^1$, p$^2$ and p$^3$ represent groups that protect hydroxyls that can be eliminated later or they can be equivalent to R$^3$ in (I), is made to react with a monosaccharide of formula (III),

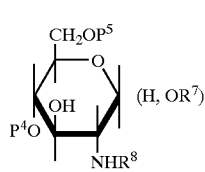

(III)

where R$^7$ can be equivalent to R$^1$ in (I) or it can be a group that may coincide or not with R$^1$, and later be eliminated so that R$^1$=H in (I), R$^8$ can be a group equivalent to R$^2$ in (I) or a group that protects amino groups, P$^4$ and P$^5$ can be protective groups, jointly constituting a cyclic protective group, either P$^4$ or P$^5$ can be acetyl, in which case P$^4$ will be equivalent to B or P$^5$ will be equivalent to A, to form a intermediate disaccharide of formula (IV):

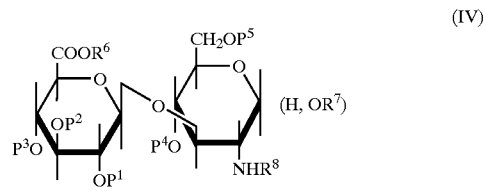

(IV)

When reactive group R$^5$ in (II) is Br, then the reaction between (II) and (III) can take place, for example, in a suitable organic solvent, preferably di-dichloromethane, at a suitable temperature, preferably room temperature, and in the presence of a catalyst, such as, for example, silver triflate, and a proton acceptor can also be present.

When reactive group R$^5$ in (II) is —O—C(=NH)—CCl$_3$, the condensation reaction between the α-imidate (II) and the alcohol (III) can take place in the presence of trimethylsilyl triflate, in a suitable organic solvent, for example dichloromethane, and preferably at room temperature.

Preferably, the p$^1$, p$^2$ and P$^3$ groups represent pivaloyl, benzoyl, acetyl or benzyl groups.

Groups p$^4$ and P$^5$ preferably represent a cyclic protective group like benzylidene, which comes from the reaction of hydroxyls 4 and 6 of the glucosamine ring with the benzaldehyde.

Group R$^6$ preferably represents methyl.

Group R$^7$ preferably represents methyl or benzyl.

Group R$^8$ preferably represents acetyl, trichloroacetyl or benzyloxycarbonyl (BOC).

The intermediate disaccharide of formula (IV) is selectively disprotected. For example, if hydroxyls 4 and 6 of the glucosamine ring are protected in the form of acetal, the disaccharide of formula (IV) can be treated for example with ethanethiol/dichloromethane in the presence of p-toluenesulphonic acid, obtaining the intermediate disaccharide of formula (V),

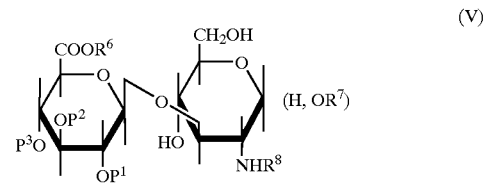

(V)

where p$^1$, p$^2$, p$^3$, R$^6$, R$^7$ and R$^8$ represent the previously described groups.

From the intermediate disaccharide of formula (V), the functional groups desired can be progressively introduced.

For example, for O-sulphonation in the C-4 of the glucosamine ring, the primary alcohol in position 6 can be protected for example with an acetyl group (in which case CH$_2$OP$^5$ will be obtained, where P$^5$=acetyl), by adding acetic anhydride in a suitable solvent such as pyridine, and a temperature of below 0° C., or with a benzoyl group, using for example benzoyl cyanide in, for example, pyridine, and then the free hydroxyl in the C-4 can be made to react with, for example, the sulfur trioxide-trimethylamine complex (SO$_3$-NMe$_3$) in, for example, N,N-dimethylformamide and at a suitable temperature, preferably between 40 and 60° C.

For O-sulphonation of the hydroxyl in C-6 of the intermediate disaccharide of formula (V) to take place, it is treated with, for example, the sulfur trioxide-trimethylamine complex (SO$_3$-NMe$_3$) in, for example, N,N-dimethylformamide, obtaining a majority of the sulphate derivative in C-6, together with a smaller proportion of the disulphate derivative. Adjusting the reaction conditions it is possible to increase the proportion of the disulphate derivative (in C-4 and in C-6 of the glucosamine ring).

Once the sulphate groups have been introduced into C-4 and/or C-6 of the glucosamine ring, if groups $p^1$, $p^2$, $p^3$, $p^4$, $p^5$, $R^6$, $R^7$ and $R^8$ are not equivalent to the relevant groups in formula (I), total or selective disprotection will be applied to obtain the compounds of formula (I), and when required, after the disprotection, the group or groups will then be made to react to obtain the compounds of formula (I).

For example, to obtain a formula (I) compound in which $R^2$ is SO$_3$M, once the sulphate group has been introduced into C-4, or C-6, or C-4 and C-6, if $R^8$ is, for example, benzyloxycarbonyl (BOC), hydrogenolysis will be performed, and the amino group obtained will later be made to react at basic pH with, for example, the sulfur trioxide-trimethylamine complex.

To obtain a compound of formula (I) in which $R^1$ is hydrogen, it is possible to start with another compound of formula (I) in which $R^1$ is benzyl, and then remove the benzyl group by hydrogenolysis, using, for example, Pd—C in the presence of a suitable solvent such as, for example, aqueous methanol.

To illustrate the described procedure, Schemes 1 and 2 show the synthetic sequences to obtain some compounds of formula (I)

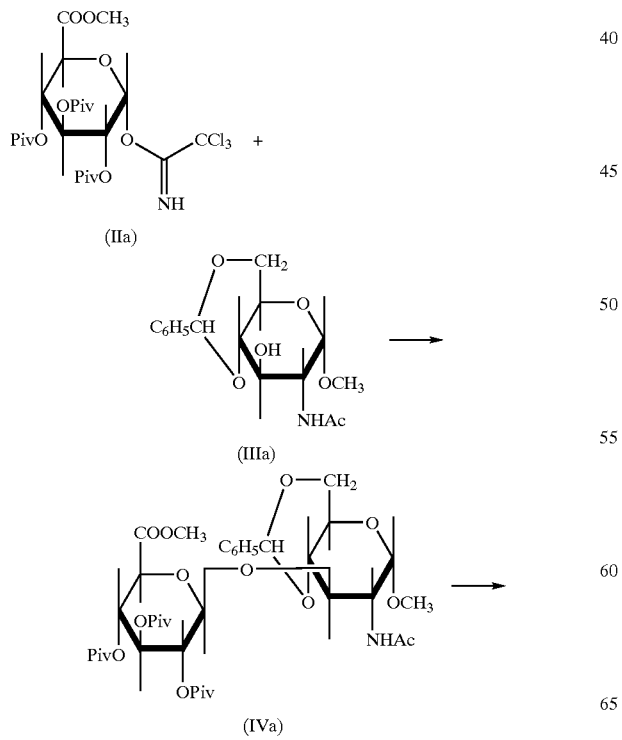

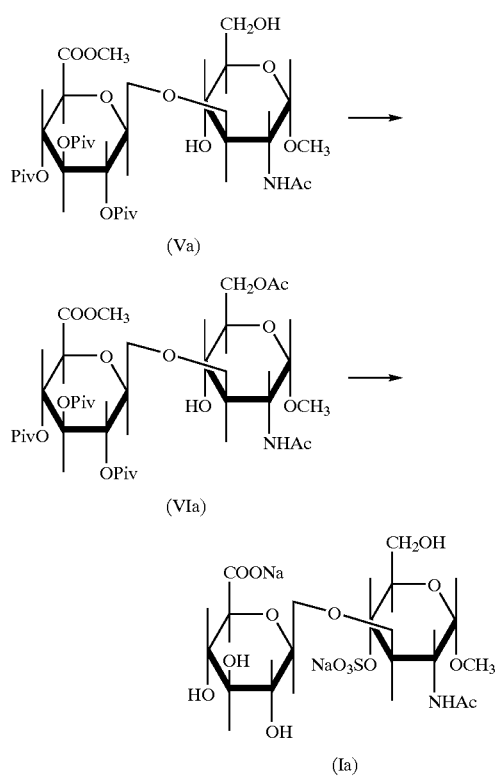

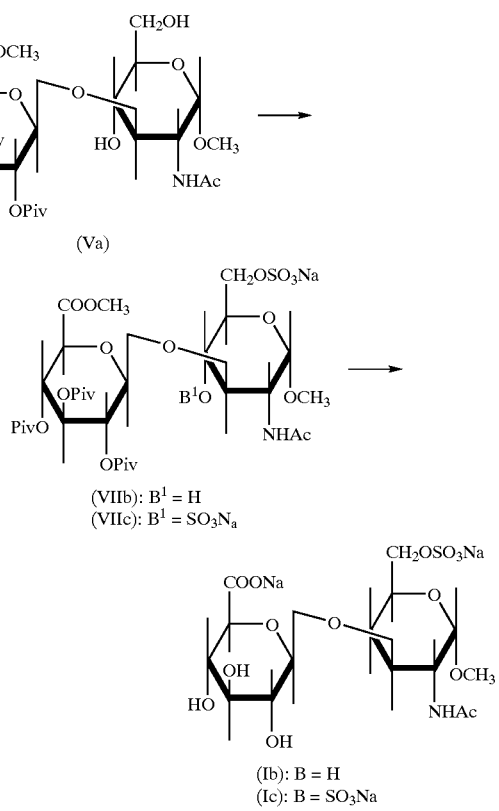

Moreover, to also illustrate the described procedure, Scheme 3 shows the synthetic sequence to obtain some compounds of formula (I) in which $R^1$ is hydrogen or benzyl.
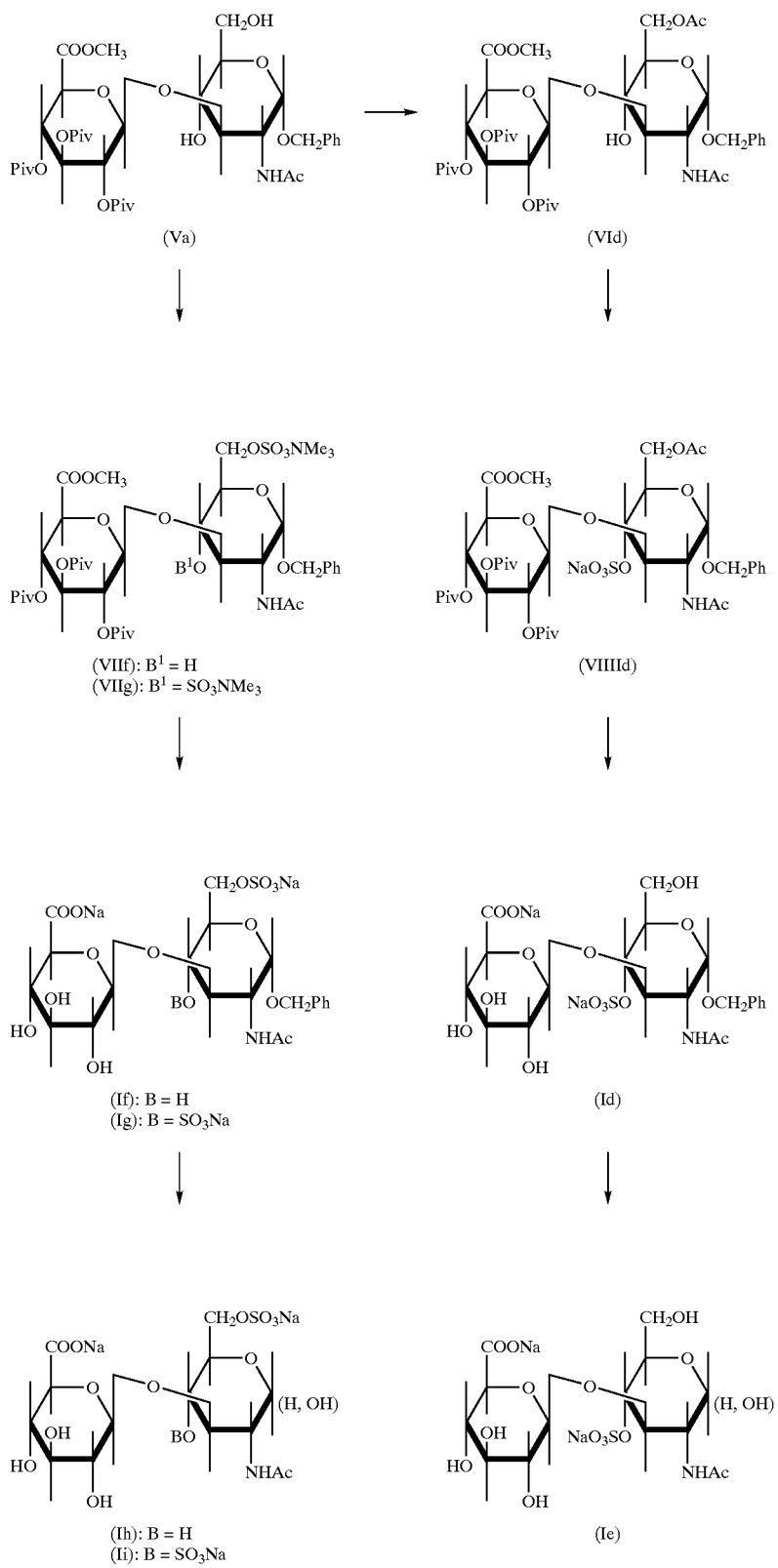
Scheme 3

The initial monosaccharide of formula (II) can be obtained from the commercial compound D-glucurono-3,6-lactone of formula (IX), by means of a sequence of reactions that are well known in carbohydrate chemistry.

To illustrate this sequence, Scheme 4 shows how the compound of formula (IIa) (II with $R^5$=—O—C(=NH)—$CCl_3$, $P^1$, $P^2$ and $P^3$=pivaloyl and $R^6$=methyl) is obtained, the synthesis of which is described in the Examples.

Scheme 4

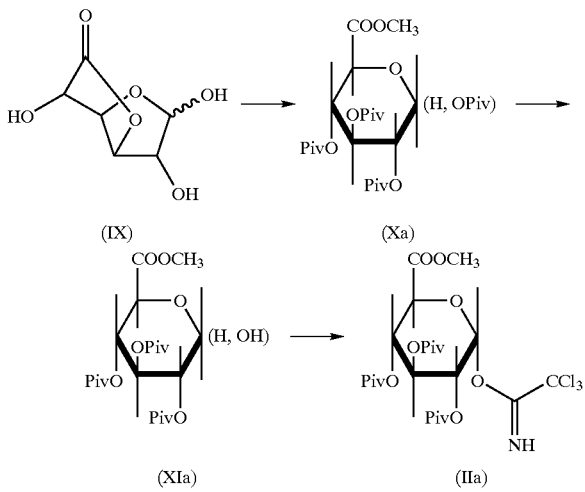

The initial monosaccharide of formula (III) can be obtained from the commercial D-glucosamine hydrochloride of formula (XII), by means of a series of selective hydroxyl protection reactions.

To illustrate this synthetic sequence, Scheme 5 shows how the compound of formula (IIIa) (compound of formula III with $P^4$ and $P^5$=benzylidene, $R^7$=methyl and $R^8$=acetyl) is obtained, the synthesis of which is described in the Examples.

If $R^7$=benzyl, the anomeric hydroxyl in compound (XIIIa) can be benzylated with benzyl alcohol, in the presence of gaseous hydrogen chloride, and at a temperature between, for example, 50 and 80° C.

Scheme 5

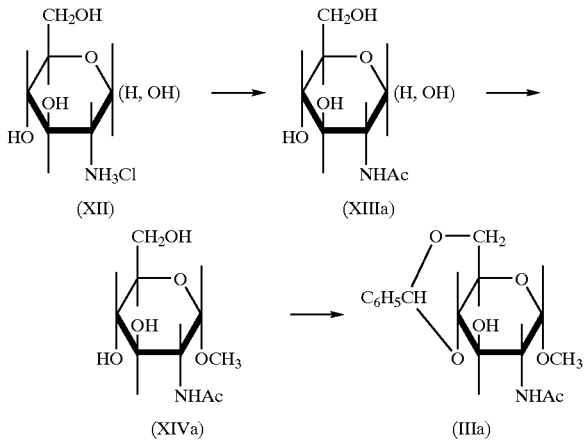

Another aspect of the present invention is its utility in human therapy, with application for the prevention or treatment of arthrosis (osteoarthritis), and inflammatory diseases such as inflammatory arthritis, rheumatoid arthritis, psoriatic arthritis, rheumatic fever, palindromic rheumatism, Reiter's syndrome, lupus eritomatosus and ankylosing spondylitis.

The compounds of the present invention can also be used to control of blood clotting.

This invention also refers to a process to prepare a drug that is effective in the prevention or treatment of arthrosis, of inflammatory diseases and blood clotting, in which said process includes mixing a pharmaceutically acceptable vehicle and a therapeutically effective quantity of a compound of formula (I).

For the therapeutic use of the compounds of the present invention, they are formulated in suitable pharmaceutical compositions, making use of conventional techniques and excipients, as described in Remington's Pharmaceutical Science Handbook, Mack Pub. Co., N.Y., USA.

The new pharmaceutical compositions of the invention can be administered to patients in suitable doses. The administration of the compositions can be performed in different ways, for example, oral, intravenous, intraperitoneal, intra-articular, subcutaneous, intramuscular, topical, intradermal or intranasal administration. The pharmaceutical compositions of the invention include a therapeutically effective quantity of one of the compounds of the invention. Said quantity depends on a large number of factors such as for example, the physical condition of the patient, age, sex, particular compound, means of administration and other well known factors. It is also understood that the active ingredient can be administered in single or multiple doses, to provide the desired therapeutic effects. If required, other therapeutic agents can be used together with those provided by the present invention.

The compounds of the invention are preferably administered to the patient in a pharmaceutically acceptable vehicle. These vehicles are well known and usually are in solid or liquid form. The pharmaceutical preparations in solid form that can be prepared from this invention include powders, pellets, tablets, dispersible granules, capsules, seals, suppositories and other solid pharmaceutical forms. The preparations in liquid form include solutions, suspensions, emulsions and micro-spheres. Preparations in solid form that can be converted, immediately before use, into preparations in liquid form, for oral, parenteral or intra-articular administration, are also contemplated. Said liquid forms include solutions, suspensions and emulsions.

One advantage of the present invention in relation to glycosaminoglycans glucosaminoglicanes such as hyaluronic acid, lies in the fact that, since the compounds of the present invention are synthetic products, there are no production limitations.

DETAILED DESCRIPTION OF THE PREFERRED EMBODIMENTS

The following examples are not exclusive, and they illustrate the preparation of the compounds of this invention.

EXAMPLE 1

Methyl 2-acetamido-2-deoxy-3-O-(β-D-glucopyranosyluronic acid)-6-O-sulfo-α-D-glucopyranoside, disodium salt (Ib)

1A Methyl 1,2,3,4-tetra-O-pivaloyl-β-D-glucopyranosyluronate (Xa)

To a sodium hydroxide 0.01 M solution in methanol (400 ml), D-glucurono-3,6-lactone (60 g, 0.288 mmol) is added, and the mixture is stirred for 1 h at room temperature. The yellow dissolution is then concentrated and the residue is dissolved in a mixture of pyridine (500 ml) and chloroform (100 ml) and cooled at 0° C. Slowly pivaloyl chloride (284 ml, 2.30 mmol) is added while stirring, continuing to stir for 6 days at room temperature. The mixture is extracted with $CH_2Cl_2$ (3×200 ml) and the organic extracts are dried with $MgSO_4$ and vacuum concentrated. This raw material is purified by column chromatography (hexane/AcOEt 12:1), obtaining 102.5 g of the product (65% yield).

NMR $^1$H (500 MHz, CDCl3) δ ppm: 5.736 (d, 1H, $J_{12}$=8 Hz, H-1), 5.403 (t, 1H, $J_{34}$=$J_{45}$=9.5 Hz, H-3), 5.249 (m, 2H, H-2, H-4), 4.16 (d, 1H, $J_{45}$=10 Hz, H-5), 3.70 (s, 3H, COOMe), 1.16, 1.11, 1.10 (3 s, 36H, 4-OPiv).

1B Methyl 2,3,4-tri-O-pivaloyl-D-glucopyranosiluronate (XIa)

A solution of methyl 1,2,3,4-tetra-O-pivaloyl-β-D-glucopyranosyluronate (40 g, 73.44 mmol) and hydrazyne acetate (13.53 g, 146.9 mmol) is dissolved in dry DMF (120 ml) and stirred for 2 h at room temperature. The mixture is diluted with ethyl acetate (100 ml) and washed with water (3×100 ml), the organic extracts are dried with MgSO$_4$ and vacuum concentrated. The resulting residue is purified by column chromatography (hexane/AcOEt 3:1) to provide 25.5 g (75% yield) of the product and 20% of the initial product.

NMR $^1$H (500 MHz, CDCl$_3$) δ ppm: β-5.40 (t, 1H, $J_{34}$=$J_{23}$=9.5 Hz, H-3), 5.23 (t, 1H, $J_{45}$=$J_{34}$=10 Hz, H-4), 4.93 (dd, 1H, $J_{12}$=8 Hz, $J_{23}$=9.5 Hz, H-2), 4.75 (d, 1H, $J_{12}$=8 Hz), 4.1 (d, 1H, $J_{34}$=10 Hz H-5), α-5.48 (d, 1H, $J_{12}$=3.5 Hz, H-1), 5.19 (t, 1H, $J_{45}$=$J_{43}$=10 Hz, H-4), 4.85 (dd, 1H, $J_{12}$=3.5 Hz, $J_{23}$=10 Hz, H-2), 4.56 (d, 1H, $J_{54}$=10 Hz, H-5), 3.67 (s, 6H, 2COOMe), 1.0 and 1.3 (3 s, 40H, 6-OPiv).

1C Methyl (2,3,4-tri-O-pivaloyl-D-glucopyranosyl trichloroacetimidate)uronate (IIa)

To a solution of methyl 2,3,4-tri-O-pivaloil-D-glucopyranosyluronate (22 g, 47.76 mmol) in dry CH$_2$Cl$_2$ (40 ml) and trichloroacetonitrile (72 ml, 716.45 mmol), 1,8-diazabicyclo(5.4.0)undec-7-ene (0.5 ml) is added, and the mixture is stirred for 30 minutes at room temperature, after which it is vacuum concentrated. The residue is purified by silica gel column chromatography (hexane/AcOEt 5:1 with 1% of NEt$_3$) to provide 22.5 g of the compound (87% yield).

NMR $^1$H (500 MHz, CDCl$_3$) δ ppm: 8.69 (s, 1H, NH), 6.58 (d, 1H, $J_{12}$=3.5 Hz, H-1), 5.63 (t, 1H, $J_{32}$=$J_{34}$=10 Hz, H-3), 5.24 (t, 1H, $J_{43}$=$J_{45}$=10 Hz, H-4), 5.12 (dd, 1H, $J_{21}$=3.5 Hz, $J_{23}$=10 Hz H-2), 4.42 (d, 1H, $J_{45}$=10 Hz, H-5), 3.62 (s, 3H, COOMe), 1.12, 1.11, 1.07 (3 s, 27H, 3-OPiv).

1D N-Acetylglucosamine (XIIIa)

D-glucosamine hydrochloride (100 g, 0.46 mol) is added to a 0.6M solution of MeONa/MeOH and stirred for 5 minutes. Acetic anhydride (48 ml) is then added, and after 30 minutes a white precipitate appears, which is filtered and washed with cold ethanol. The liquor is recrystallised from absolute ethanol, obtaining 79.3 g of the compound (quantitative).

NMR $^1$H (300 MHz, D$_2$O) δ ppm: 5.06 (d, 1H, $J_{12}$=3.44 Hz, H-1), 3.76–3.53 (m, 5H, H-2, H-3, H-4, H-6, H-6'), 3.27 (m, 1H, H-5), 1.90 (s, 3H, CH$_3$CONH—).

1E Methyl 2-acetamido-2-deoxy-α-D-glucopyranoside (XIVa)

To a solution of N-acetylglucosamine (50 g, 0.22 mmol) in MeOH (50 ml), a catalytic quantity of Amberlite IR-120 H$^+$ resin is added, and the mixture is heated for 2 days. The mixture is filtered, concentrated and purified by silica gel column chromatography (CH$_2$Cl$_2$/MeOH 5:1), obtaining 10 g of the α-anomer methyl 2-acetamido-2-deoxy-α-D-glucopyranoside (25%) anomer and 40 g of the β-anomer that is isomerised to give the α-anomer methyl 2-acetamido-2-deoxy-α-D-glucopyranoside in the same reaction conditions (70% yield).

NMR $^1$H (300 MHz, CD$_3$OD) δ ppm: 4.64 (d, 1H, $J_{12}$=3.5 Hz, H-1), 3.89 (dd, 1H, $J_{21}$=3.5 Hz, $J_{23}$=8.8 Hz, H-2), 3.81 (dd, 1H, $J_{65}$=2.5 Hz, $J_{66'}$=12 Hz, H-6), 3.67 (dd, 1H, $J_{6'5}$=5 Hz, $J_{66'}$=12 Hz H-6'), 3.62 (dd, 1H, $J_{34}$=10.5 Hz, $J_{32}$=8.5 Hz H-3), 3.36 (s, 3H, MeO), 3.29 (m, 1H, H-4), 1.96 (s, 3H, CH$_3$CONH—).

1F Methyl 2-acetamido4,6-benzylidene-2-deoxy-α-D-glucopyranoside (IIIa)

To a solution of methyl 2-acetamido-2-deoxy-α-D-glucopyranoside (0.88 g, 3.74 mmol) in dry DMF (10 ml), p-toluenesulphonic acid in catalytic quantities, and PhCH(OMe)$_2$ (1.014 ml, 5.61 mmol) are added, and the mixture is heated for 12h at a temperature of 55° C. Then the mixture is neutralised with a saturated NaHCO$_3$ solution, diluted with CH$_2$Cl$_2$ and washed with water (2×50 ml). The organic extracts are dried with MgSO$_4$ and vacuum concentrated. The resulting raw material is purified in a silica gel column (CH$_2$Cl$_2$/MeOH 25:1) to give 1.079 g of the compound (90% yield).

NMR $^1$H (500 MHz, CDCl$_3$) δ ppm: 7.5–7.3 (m, 5H, Ph), 5.83 (d, 1H, $J_{NH,2}$=8.5 Hz, NH—), 5.55 (s, 1H, $H_{ipso}$), 4.70 (d, 1H, $J_{12}$=3.5 Hz, H-1), 4.27 (dd, 1H, $J_{65}$=3.5 Hz, $J_{66'}$=12 Hz H-6), 4.21 (ddd, 1H, $J_{21}$=3.5 Hz, $J_{2,NH}$=8.5 Hz, $J_{23}$=9 Hz H-2), 3.89 (ddd, 1H, $J_{3,OH}$=3.5 Hz, $J_{34}$=$J_{32}$=9 Hz H-3), 3.76 (m, 1 H, H-5, H-6'), 3.57 (t, 1H, $J_{43}$=$J_{45}$=9 Hz H-4), 3.40 (s, 3H, MeO), 2.97 (d, 1H, $J_{3,OH}$=3.5 Hz, OH), 2.06 (s, 3H, CH$_3$CONH—).

1G Methyl 2-acetamido-4,6-benzylidene-2-deoxy-3-O-(methyl 2,3,4-tri-O-pivaloyl-β-D-glucopyranosyluronate)-α-D-glucopyranoside (IVa)

To a mixture of methyl (2,3,4-tri-O-pivaloyl-D-glucopyranosyl trichloroacetimidate)uronate (10 g, 16.54 mmol) and methyl 2-acetamido-4,6-benzylidene-2-deoxy-α-D-glucopyranoside (4.1 g, 12.73 mmol) dissolved in dry CH$_2$Cl$_2$ (80 ml) at room temperature, trimethylsilyl trifluoromethanesulphonate (0.3 ml, 0.1 eq.) is added, and the mixture is stirred for 1 h. The reaction is then neutralised adding saturated NaHCO$_3$ solution, and diluted with CH$_2$Cl$_2$, and the organic phase is washed with H$_2$O (3×100 ml). The organic extracts are dried with MgSO$_4$ and vacuum concentrated. The raw material obtained is purified by silica gel column chromatography (toluene/acetone 5:1), obtaining 7.8 g of methyl 2-acetamido4,6-benzylidene-2-deoxy-3-O-(methyl 2,3,4-tri-O-pivaloyl-β-D-glucopyranosyluronate)-D-glucopyranoside (80% yield) and 1.4 g (14%) of recovered methyl 2-acetamido-4,6-benzylidene-2-deoxy-α-D-glucopiranoside.

NMR $^1$H (500 MHz, CDCl$_3$) δ ppm: 7.5–7.3 (m, 5H, Ph), 5.59 (d, 1H, $J_{NH,2}$=7 Hz, NH—), 5.5 (s, 1H, $H_{ipso}$), 5.22 (t, 1H, $J_{34}$=$J_{32}$=9.5 Hz, H-3), 5.1 (t, 1H, $J_{43}$=$J_{45}$=9.5 Hz H4), 4.97 (t, 1H, $J_{21}$=8 Hz, H-2), 4.88 (d, 1H, $J_{12}$=3 Hz, H-1'), 4.87 (d, 1H, $J_{12}$=8 Hz, H-1), 4.22 (m, 1H, H-5'), 4.11 (m, 1H, H-2'), 3.92 (t, 1H, $J_{34}$=$J_{32}$=9 Hz, H-3'), 3.82 (t, 1H, $J_{34}$=$J_{32}$=9 Hz, H-4'), 3.76 (m, 2H, H-5, H-6'), 3.70 (m, 1H, H-6'), 3.64 (s, 3H, COOMe), 3.32 (s, 3H, OMe), 2.00 (s, 3H, MeCONH—), 1.4–1.0 (3 s, 27H, 3-OPiv).

1H Methyl 2-acetamido-2-deoxy-3-O-(methyl 2,3,4-tri-O-pivaloyl-β-D-glucopyranosyluronate)-α-D-glucopyranoside (Va)

To a solution of methyl 2-acetamido-4,6-benzylidene-2-deoxy-3-O-(methyl 2,3,4-tri-O-pivaloyl-β-D-glucopyranosyluronate)-α-D-glucopiranoside (100 mg, 0.13 mmol) in dry CH$_2$Cl$_2$ (2 ml) and containing a catalytic quantity of p-toluenesulphonic acid, EtSH (48 μl 0.65 mmol) is slowly added, and is stirred at room temperature for 5 h. It is then neutralised by adding saturated NaHCO$_3$ solution, diluted with CH$_2$Cl$_2$ (25 ml), and the organic phase is washed with H$_2$O (2×25 ml). The organic extracts are dried with MgSO$_4$ and vacuum concentrated. The resulting raw material is purified by silica gel column chromatography (CH$_2$Cl$_2$/MeOH 25:1), obtaining 78.4 mg of the compound (89% yield).

NMR $^1$H (500 MHz, CDCl$_3$) δ ppm: 5.89 (d, 1H, $J_{NH,2}$=7 Hz, NH), 5.34 (t, 1H, $J_{34}$=$J_{32}$=9.5 Hz, H-3), 5.27 (t, 1H, $J_{43}$=$J_{45}$=9 Hz H-4), 4.88 (t, 1H, $J_{21}$=5 Hz, H-2), 4.80 (d, 1H, $J_{12}$=6 Hz, H-1), 4.68 (d, 1H, $J_{12}$=3.5 Hz, H-1'), 4.16

(d, 1H, $J_{54}$=9.5 Hz H-5), 4.07 (m, 1H, H-2), 3.86 (dd, 1H, $J_{65}$=6 Hz, $J_{66'}$=12 Hz, H-6'), 3.77 (dd, 1H, J $_{6'5}$=5 Hz, $J_{6'6}$=12 Hz, H-6), 3.71 (s, 3H, COOMe), 3.70 (m, 1H, H-3'), 3.57 (t, 1H, H4'), 3.56 (m, 1H, H-3'), 3.31 (s, 3H, OMe), 2.00 (s, 3H, MeCONH—), 1.4–1.0 (3 s, 27H, 3-OPiv).

1I Methyl 2-acetamido-2-deoxy-3-O-(methyl 2,3,4-tri-O-pivaloyl-β-D-glucopyranosyluronate)-4,6-disulfo-α-D-glucopiranoside, disodium salt (VIIc)

Methyl 2-acetamido-2-deoxy-3-O-(methyl 2,3,4-tri-O-pivaloyl-β-D-glucopyranosyluronate)-6-sulfo-αD-glucopiranoside, sodium salt (VIIb)

A solution of methyl 2-acetamido-2-deoxy-3-O-(methyl 2,3,4-tri-O-pivaloyl-β-D-glucopyranosyluronate)-α-D-glucopyranoside (75 mg, 0.11 mmol) in dry DMF (2 ml) is stirred for 2 days in the presence of the $SO_3$—$NMe_3$ complex (200 mg, 1.437 mmol) at 55° C. in an argon atmosphere. The mixture is cooled and MeOH (1 ml) and $H_2O$ (1 ml) are added. The solution is passed through a Sephadex LH-20 column ($CH_2Cl_2$/MeOH 1:1). The fractions obtained containing the two disaccharides are concentrated and passed through a silica gel column (AcOEt/MeOH 5:1.) to separate the mono- from the disulphated. The two resulting fractions are passed through DOWEX-50 W X4 ($Na^+$) (MeOH/$H_2O$ 9:1) to give methyl 2-acetamido-2-deoxy-3-O-(methyl 2,3,4-tri-O-pivaloyl-β-D-glucopyranosyluronate)-6-sulfo-α-D-glucopyranoside, sodium salt (62.4 mg, 68% yield) and methyl 2-acetamido-2-deoxy-3-O-(methyl 2,3,4-tri-O-pivaloyl-β-D-glucopyranosyluronate)-4,6-disulfo-α-D-glucopiranoside, disodium salt (13 mg, 15% yield).

NMR $^1$H (500 MHz, $CDCl_3$) of methyl 2-acetamido-2-deoxy-3-O-(methyl 2,3,4-tri-O-pivaloyl-β-D-glucopyranosyluronate)-6-sulfo-α-D-glucopyranoside (VIIb), sodium salt δ ppm: 5.35 (t, 1H, $J_{34}$=$J_{32}$=9.5 Hz, H-3), 5.17 (t, 1H, $J_{43}$=$J_{45}$=9 Hz H-4), 5.00 (m, 2H, H-2, H-1), 4.61 (d, 1H, $J_{12}$=6 Hz, H-1'), 4.34 (dd, 1H, $J_{65}$=2 Hz, $J_{66'}$=10.5 Hz H-6'), 4.27 (d, 1H, $J_{54}$=10 Hz H-5), 4.10 (dd, 1H, $J_{65}$=6 Hz, $J_{66'}$=11 Hz H-6'), 3.94 (m, 2H, H-2', H-3'), 3.79 (m, 1H, H-5'), 3.74 (s, 3H, COOMe), 3.41 (m, 2H, H-2, H-4'), 3.38 (s, 3H, OMe), 1.97 (s, 3H, MeCONH—), 1.2–1.0 (3 s, 27H, 3-OPiv).

NMR $^1$H (500 MHz, $CDCl_3$) of methyl 2-acetamido-2-deoxy-3-O-(methyl 2,3,4-tri-O-pivaloyl-β-D-glucopyranosyluronate)-4,6-disulfo-α-D-glucopyranoside (VIIc), disodium salt δ ppm: 7.80 (d, 1H, $J_{NH,2}$=9 Hz, NH), 5.38 (t, 1H, $J_{34}$=$J_{32}$=9 Hz, H-3), 5.22 (t, 1H, $J_{43}$=$J_{45}$=10 Hz H-4), 5.11 (d, 1H, $J_{12}$=7.5 Hz, H-1), 5.01 (dd, 1H, $J_{21}$=8 Hz, $J_{23}$=9.5 Hz H-2), 4.68 (d, 1H, $J_{12}$=3 Hz, H-1'), 4.57 (d, 1H, $J_{45}$=$J_{43}$=9.5 Hz H-4'), 4.28 (m, 2H, H-6, H-5), 4.14 (m, 3H, H-3, H-5, H-6'), 4.10 (m, 1H, H-2'), 3.73 (s, 3H, COOMe), 3.41 (s, 3H, OMe), 2.05 (s, 3H, MeCONH—), 1.2–1.0 (3 s, 27H, 3-OPiv).

1J Methyl 2-acetamido-2-deoxy-3-O-(β-D-glucopyranosyluronic acid)-6-O-sulfo-α-D-glucopyranoside, disodium salt (Ib)

To a solution of methyl 2-acetamido-2-deoxy-3-O-(methyl 2,3,4-tri-O-pivaloyl-β-D-glucopyranosyluronate)-6-sulfo-α-D-glucopyranoside, sodium salt (60 mg, 0.07 mmol) in 2 ml of a (MeOH/$H_2O$ 5:1) mixture, 1.5 ml of a 3M sodium hydroxide solution is added, and is stirred at room temperature for 2 days. It is then neutralised with acetic acid to pH 8 and vacuum concentrated, and the resulting raw material is purified by Sephadex G-10 ($H_2O$/EtOH 9:1) column chromatography, obtaining 40 mg (quantitative yield) of the compound as a white solid with a melting point of 250° C. with dec.

IR (KBr): 3429, 2915, 1627, 1553, 1422, 1381, 1232, 1106, 1061, 950, 820 $cm^{-1}$.

NMR $^1$H (500 MHz, D2O) δppm: 4.76 (d, 1H, $J_{12}$=3.5 Hz, H-1'), 4.52 (d, 1H, $J_{12}$=8 Hz, H-1), 4.37 (dd, 1H, $J_{56}$=2 Hz, $J_{66}$'=11.5 Hz, H-6), 4.29 (dd, 1H, $J_{6'5}$=5.5 Hz, J66'= 11.5 Hz H-6'), 4.15 (dd, 1H, $J_{21}$=3.5 Hz, $J_{23}$=10.5 Hz H-2'), 3.94 (m, 2H, H-5', H-3'), 3.73 (m,$_1$H, H-4), 3.63 (t, 1H, $J_{43}$=$J_{45}$=9.5 Hz, H-4'), 3.53 (m, 2H, H-3, H-5), 3.45 (s, 3H, MeO), 3.37 (dd, 1H, $J_{21}$=8 Hz, $J_{23}$=9.5 Hz H-2),1.94 (s, 3H, $CH_3$CONH—).

EXAMPLE 2

Methyl 2-acetamido-2-deoxy-3-O-(β-D-glucopyranosyluronic acid)-4,6-di-O-sulfo-α-D-glucopyranoside, trisodium salt (Ic)

To a solution of methyl 2-acetamido-2-deoxy-3-O-(methyl 2,3,4-tri-O-pivaloyl-β-D-glucopyranosyluronate)-4,6-disulfo-α-D-glucopyranoside, disodium salt (13 mg, 0.01 mmol) in 2 ml of a (MeOH/$H_2O$ 5:1) mixture, 1.5 ml of a 3M sodium hydroxide solution is added, and is stirred at room temperature for 2 days. It is then neutralised with acetic acid to pH 8 and vacuum concentrated, and the resulting raw material is purified by Sephadex G-10 ($H_2O$/EtOH 9:1) column chromatography, obtaining 8.5 mg (92% yield) of the compound as a white solid with a melting point of 249–250° C. with dec.

IR (KBr): 3436, 2918, 1632, 1555, 1429, 1381, 1257, 1109, 1060, 950, 811 $cm^{-1}$.

NMR $^1$H (300 MHz, $D_2O$) δ ppm: 4.80 (m, 2H, H-1, H-1'), 4.19 (t, 1H, $J_{43}$ =$J_{45}$=9 Hz, H4'), 3.98 (t, 1H, $J_{34}$=$J_{32}$=9.3 Hz H-3'), 3.75 (m, 3H, H-6, H-6', H-5'), 3.57 (m, 1H, H-5), 3.42 (m, 2H, H-4, H-3), 3.31 (s, 4H, H-2, MeO), 2.95 (dd, 1H, $J_{21}$=3.6 Hz, $J_{23}$=10.2 Hz H-2'), 1.83 (s, 3H, $CH_3$CONH—).

EXAMPLE 3

Methyl 2-acetamido-2-deoxy-3-O-(β-D-glucopyranosyluronic acid)-4-O-sulfo-α-D-glucopyranoside, disodium salt (Ia)

3A Methyl 2-acetamido-6-O-acetyl-2-deoxy-3-O-(methyl 2,3,4-tri-O-pivaloyl-β-D-glucopyranosyluronate)-α-D-glucopyranoside (VIa)

To a solution of methyl 2-acetamido-2-deoxy-3-O-(methyl 2,3,4-tri-O-pivaloyl-β-D-glucopyranosyluronate)-α-D-glucopyranoside (100 mg, 0.147 mmol) in pyridine (2 ml) at –10° C., 0.016 ml of acetic anhydride (0.162 mmol) is added and leaved at that temperature for 2 days. $CH_2Cl_2$ is then added and the organic phase is washed with $H_2O$ (2×25 ml). The organic extracts are dried with $MgSO_4$ and vacuum concentrated. The raw material is purified by silica gel column chromatography ($CH_2Cl_2$/MeOH 40:1), obtaining 73 mg of the compound (70% yield), plus 14.6 mg of the initial product (15% yield).

NMR $^1$H (500 MHz, $CDCl_3$) δ ppm: 6.16 (d, 1H, $J_{NH,2}$=8.5 Hz, NH), 5.23 (t, 1H, $J_{34}$=$J_{32}$=9 Hz, H-3), 5.12 (t, 1H, $J_{43}$=$J_{45}$=9 Hz H-4), 4.84 (t, 1H, $J_{21}$=$J_{23}$=8 Hz H-2), 4.75 (d, 1H, $J_{12}$=6.5 Hz, H-1), 4.56 (d, 1H, $J_{12}$=3.5 Hz H-1'), 4.39 (dd, 1H, $J_{6'5}$=1.5 Hz, $J_{6'6}$=11.5 Hz H-6), 4.12 (dd, 1H, $J_{65}$=5.5 Hz, $J_{6'6}$=12 Hz H-6', H-6), 4.076 (d, 1H, $J_{54}$=10 Hz H-5), 3.96 (m, 1H, H-2'), 3.92 (d, 1H, H-5'), 3.62 (t, 1H, $J_{32}$ =$J_{34}$=8.5 Hz H-3'), 3.57 (s, 1 H, OH), 3.58 (s, 3H, COOMe), 3.38 (t, 1H, $J_{45}$=$J_{43}$=10 Hz H-4'), 3.31 (s, 3H, OMe), 1.95 (s, 3H, MeCONH—), 1.85 (s, 3H, MeCO), 1.4–1.0 (3 s, 27H, 3-OPiv).

3B Methyl 2-acetamido-6-O-acetyl-3-O-(methyl 2,3,4-tri-O-Pivaloyl-β-D-glucopyranosyluronate)-4-O-sulfo-α-D-glucopyranoside A solution of methyl 2-acetamido-6-O-acetyl-2-deoxy-3-O(methyl 2,3,4-tri-O-pivaloyl-β-D-glucopyranosyluronate)-α-D-glucopyranoside (1 g, 1.39 mmol) in dry DMF (15 ml) is stirred for 24 hours in the presence of the $SO_3$—$NMe_3$ complex (1.93 g, 13.90 mmol) at 55° C. in an argon atmosphere. The mixture is cooled and MeOH (10 ml) and $H_2O$ (5 ml) are added. The solution is passed through a Sephadex LH-20 column ($CH_2Cl_2$/MeOH 1:1). The reaction mixture containing three products is purified by silica gel column chromatography ($CH_2Cl_2$/MeOH 15:1), obtaining the following fractions: a) initial product with ammonium salts, b) intermediate $R_f$ product without sulphate and with two acetyl groups, c) lower $R_f$ product that corresponds to the title product (500 mg).

3C Methyl 2-acetamido-2-deoxy-3-O-(β-D-glucopyranosyluronic acid)-4-O-sulfo-α-D-glucopyranoside, disodium salt (Ia)

Following the same procedure already described for compounds Ib and Ic, the methyl 2-acetamido-6-O-acetyl-3-O-(methyl 2,3,4-tri-O-pivaloyl-β-D-glucopyranosyluronate)-4-O-sulfo-α-D-glucopyranoside compound is subjected to basic hydrolysis, giving rise to the title compound as a white solid with a melting point of 203° C. with dec.

IR (KBr): 3430, 2958, 1622, 1553, 1484, 1413, 1361, 1229, 1112, 1049, 904, 803 $cm^{-1}$.

NMR $^1H$ (500 MHz, $D_2O$) δ ppm: 4.74 (m, 2H, $J_{12}$=3.5 Hz, $J_{12}$=8 Hz H-1, H-1'), 4.24 (t, 1H, $J_{43}$=$J_{45}$=9 Hz, H-4), 4.02 (t, 1H, $J_{43}$=$J_{32}$ =9 Hz H-3), 3.89 (m, 1H, H-6), 3.80 (m, 2H, H-5', H-6'), 3.65 (m, 1H, H-5), 3.48 (m, 2H, H-4, H-3), 3.34 (s, 4H, H-2, MeO), 2.99 (dd, 1H, $J_{21}$=3.5 Hz, $J_{23}$=10 Hz H-2'), 1.87 (s, 3H, $CH_3CONH$—).

Pharmacological Activity

1. Introduction

The primary cause of the pathological destruction of the cartilage is the high proteolitic activity. Metalloproteases are a type of enzymes working in the degradation of the extracellular matrix. These enzymes have a big capacity to degrade the collagen triple helix. High levels of collagenase have been found in the cartilage of patients with osteoarthritis (OA) and also a relationship between its levels and the severity of the osteoarthritic lesions.

Even if it is still unknown the OA ethiology, it is accepted that the first alterations are produced at the chondrocyte level because of a loss of equilibrium between the synthesis and degradation of the extracellular matrix of the articular cartilage. The final result is an accelerated destruction of the extracellular matrix, mainly by the proteolytic enzymes from the chondrocytes and the synovial cells, followed by alterations in the repairing systems of the cartilage.

The effect of two different compounds of the invention on the equilibrium of the different constituents of the extracellular matrix was studied. Specifically, here constituents able to promote the synthesis of the cartilage (aggrecan and collagen type II) and able to reduce its degradation (IL-1α, IL-1β, matrix metalloproteinase MMP-13 or collagenase type 3) have been analysed.

2. Experimental Design

Human articular chondrocytes were obtained from knees of 3 different donors (F16, F53, F73: F16=16-years-old female; F53=53-years-old female; F73=73-years-old female). Each of the compounds (Ib, IC) has been tested on human articular cartilage chondrocytes obtained from 2 different donors. The chondrocytes were cultured over 7 days in alginate gel and during this period they were exposed to the different drugs. The cells were then isolated from the gel and tested. The test protocol specified that the chondrocytes were exposed to IL-1 since it has been shown that particularly IL-1-treated chondrocytes, as opposed to non-treated chondrocytes, respond to polysulphated polysaccharides. As a positive control, chondroitin sulphate (CS) and chondroitin polysulphate (CPS) have been used.

The accumulation of aggrecan and of type II collagen in the cell-associated matrix (CAM) of the chondrocytes in culture was the primary variable to evaluate the DMOAD (Disease Modifying Osteoarthritic Drug) effects of the 2 compounds. The intracellular levels of IL-1α and β, MMP-13 were also studied.

All assays were made by flow cytometry. Specific Fluoresceine Isothiocyanate- (FITC-) or Phycoerythin (PE-) conjugated monoclonal antibodies (Mab) against the different proteins have been used. The results were expressed as Mean Fluorescence Intensity (MFI) of the chondrocyte population after staining with the respective Mab.

3. Results

Tables 1 and 2 show activity values found for the compounds of the present invention.

TABLE 1

FARMACOLOGY ACTIVITY OF Ib

| | AGGR | COLL | IL-1α | IL-1β | MMP-13 |
|---|---|---|---|---|---|
| F16 + IL-1β | 37.90 | 1.46 | 25.88 | 2.24 | 31.54 |
| F16 + IL-1β + CS(10 µ/ml) | 47.39 | 2.97 | 17.09 | 1.17 | 23.34 |
| F16 + IL-1β + CPS(10 µ/ml) | 46.41 | 2.31 | 16.94 | 1.18 | 23.20 |
| F16 + IL-1β + Ib(25 µ/ml) | 48.77 | 2.92 | 19.83 | 1.03 | 22.49 |
| F53 + IL-1β | 11.03 | 0.67 | 49.92 | 4.59 | 22.04 |
| F53 + IL-1β + CS(10 µ/ml) | 15.09 | 1.23 | 45.41 | 3.06 | 14.70 |
| F53 + IL-1β + CPS(10 µ/ml) | 19.47 | 2.12 | 43.84 | 2.68 | 11.82 |
| F53 + IL-1β + Ib(25 µ/ml) | 14.41 | 1.00 | 44.24 | 2.92 | 17.67 |

AGGR = AGGRECAN
COLL = TYPE II COLLAGEN
Each value of the table is the average of three mesures

TABLE 2

FARMACOLOGY ACTIVITY OF Ic

| | AGGR | COLL | IL-Iα | IL-1β | MMP-13 |
|---|---|---|---|---|---|
| F53 + IL-1β | 11.03 | 0.67 | 49.92 | 4.59 | 22.04 |
| F53 + IL-1β + CS(10 µg/ml) | 15.09 | 1.23 | 45.41 | 3.06 | 14.70 |
| F53 + IL-1β + CPS(10 µg/ml) | 19.47 | 2.12 | 43.84 | 2.68 | 11.82 |
| F53 + IL-1β + Ic(25 µg/ml) | 18.42 | 0.97 | 44.69 | 3.63 | 19.62 |
| F73 + IL-1β | 14.29 | 1.28 | 26.97 | 1.92 | 27.18 |
| F73 + IL-1β + CS(10 µg/ml) | 28.72 | 1.45 | 17.49 | 0.47 | 21.12 |
| F73 + IL-1β + CPS(10 µg/ml) | 24.71 | 1.96 | 16.43 | 0.45 | 22.11 |
| F73 + IL-1β + Ic(25 µg/ml) | 59.82 | 2.45 | 14.92 | 0.45 | 18.92 |

AGGR = AGGRECAN
COLL = TYPE II COLLAGEN
Each value of the table is the average of three mesures The IL-1 +chondrocytes treated with CS or CPS, compared to the untreated ones, showed a statistically significant increase in the accumulation of aggrecan and of type II collagen ($p<0.05$) in the CAM. They also showed a statistically significant decrease in the levels of IL-1α, IL-1β and MMP-13 ($p<0.05$).

When the IL-1+chondrocytes were treated with any of the two compounds of the present invention, a statistically significant increase in the accumulation of aggrecan and of type II collagen ($p<0.01$) and a significant decrease in the levels of IL-1α, IL-1β and MMP-13 ($p<0.05$) was also observed.

4. Conclusion

Both Ib and Ic possess 'cartilage structure modifying effects'. Their effects are comparable to those of Chondroitin Sulfate (CS) and Chondroitin Polysulphate (CPS).

What is claimed is:

1. A disaccharide having anti-arthrosic properties represented by formula (I), a solvate or pharmaceutically acceptable salt thereof:

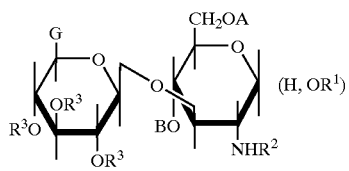
(I)

wherein:
$R^1$ is selected from the group consisting of hydrogen, linear or branched ($C_1$–$C_4$)-alkyl, phenylalkyl of less than ten carbon atoms and —$COCH_3$;

$R^2$ is selected from the group consisting of hydrogen, —$COCH_3$ and $SO_3M$;

$R^3$ is selected from the group consisting of hydrogen, linear or branched ($C_1$–$C_4$)-alkyl, phenylalkyl of less than ten carbon atoms, —$COCH_3$ and —COPh, wherein Ph is phenyl;

G is —$COOR^4$ or —COOM, wherein $R^4$ is selected from the group consisting of hydrogen, ($C_1$–$C_2$)-alkyl and arylalkyl of less than sixteen carbon atoms;

A is selected from the group consisting of hydrogen, —$SO_3H$, —$SO_3M$ and —$COCH_3$; and B is selected from the group consisting of hydrogen, —$SO_3H$, —$SO_3M$, and —$COCH_3$, wherein at least one of A or B is —$SO_3H$ or —$SO_3M$, wherein M is an organic or metallic cation.

2. The disaccharide according to claim 1, wherein G is —$COOR^4$ or —COOM, wherein $R^4$ is ($C_1$–$C_2$)-alkyl, or arylalkyl of less than sixteen carbon atoms and M is a metallic cation.

3. The disaccharide according to claim 2, wherein $R^1$ is hydrogen, $R^2$ is —$COCH_3$ and $R^3$ is hydrogen.

4. The disaccharide according to claim 2, wherein $R^1$ is methyl, $R^2$ is —$COCH_3$ and $R^3$ is hydrogen.

5. The disaccharide according to claim 3 or claim 4, wherein A is hydrogen and B is —$SO_3M$, and M is a metallic cation.

6. The disaccharide according to claim 3 or claim 4, wherein A is —$SO_3M$, and B is hydrogen, and M is a metallic cation.

7. The disaccharide according to claim 3 or claim 4 wherein A and B are each —$SO_3M$, and M is a metallic cation.

8. The disaccharide according to claim 1, wherein M is a sodium cation.

9. The disaccharide according to claim 1, wherein said disaccharide is selected from the group consisting of methyl 2-acetamido-2-deoxy-3-O (β-D-glucopyranosyluronic acid) -6-O-sulfo-α-D-glucopyranoside, disodium salt;

methyl 2-acetamido-2-deoxy-3-O- (β-D-glucopyranosyluronic acid) -4-O-sulfo-β-D-glucopyranoside, disodium salt;

methyl 2-acetamido-2-deoxy-3-O-(β-D-glucopyranosyluronic acid) -4,6-di-O-sulfo-α-D-glucopyranoside, trisodium salt;

2-acetamido-2-deoxy-3-O- (β-D-glucopyranosyluronic acid) -6-O-sulfo-D-glucopyranose, disodium salt;

2-acetamido-2-deoxy-3-O- (β-D-glucopyranosyluronic acid) -4-O-sulfo-D-glucopyranose, disodium salt; and 2-acetamido-2-deoxy-3-O- (β-D-glucopyranosyluronic acid) -4,6-di-O-sulfo-D-glucopyranose, trisodium salt.

10. A process for preparing a disaccharide represented by formula (I) of claim 1, comprising the steps of:

(a) reacting a monosaccharide represented by formula (II) with a monosaccharide represented by formula (III) so as to form an intermediate disaccharide represented by formula (IV):

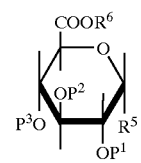
(II)

wherein:
$R^5$ is a reactive group that establishes a β-(1→3) bond with the free hydroxyl group in the monosaccharide represented by formula (III), $R^6$ is selected from the group consisting of hydrogen, ($C_1$–$C_2$)-alkyl, arylalkyl of less than sixteen carbon atoms and a group that protects a carboxyl group and can subsequently be eliminated, $P^1$, $P^2$ and $P^3$ are each independently selected from the group consisting of a group that protects a hydroxyl group and can subsequently be eliminated, hydrogen, linear or branched ($C_1$–$C_4$)-alkyl, phenylalkyl of less than ten carbon atoms, —$COCH_3$ and —COPh, wherein Ph is phenyl

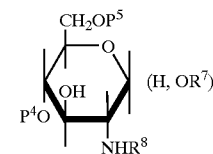
(III)

wherein $R^7$ is selected from the group consisting of hydrogen, linear or branched ($C_1$–$C_4$)-alkyl, phenylalkyl of less than ten carbon atoms, —$COCH_3$ and a group different than $R^1$, and be subsequently eliminated so that $R^1$ =H in formula (I), $R^8$ is selected from the group consisting of hydrogen, —$COCH_3$, $SO_3M$ and a group that protects an amino group, $P^4$ and $P^5$ are each a protective group or jointly form a cyclic protective group, wherein when either $P^4$ or $P^5$ is acetyl, $P^4$ is selected from the group consisting of hydrogen, —$SO_3H$, —$SO_3M$ and —$COCH_3$ or $P^5$ is —$SO_3H$, —$SO_3M$, and —$COCH_3$,

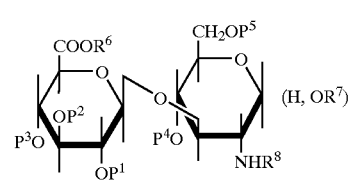
(IV)

b) selectively deprotecting the resulting disaccharide represented by formula (IV) so as to obtain an intermediate disaccharide represented by formula (V),

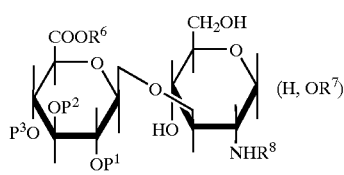 (V)

wherein $P^1$, $P^2$, $P^3$, $R^6$, $R^7$ and $R^8$ are as defined above;

(c) introducing a sulphate group or groups into the glucosamine ring of the resulting intermediate disaccharide represented by formula (V), wherein for O-sulphonation of the hydroxyl group in the C-4 position of the glucosamine ring, the hydroxyl group in position 6 is protected, wherein for O-sulphonation of the hydroxyl group in the C-6 position of the glucosamine ring, the hydroxyl groups in positions 4 and 6 are not protected, or wherein for O-sulphonation of the hydroxyl groups in the C-4 and C-6 positions of the glucosamine ring, the hydroxyl groups in positions 4 and 6 are not protected; and (d) optionally, totally or selectively deprotecting so as to obtain a disaccharide represented by formula (I), and optionally, after deprotecting, the group or groups are reacted so as to obtain a disaccharide represented by formula (I).

11. A process for preparing a drug effective in the prevention or treatment of arthrosis, inflammatory diseases and blood clotting, comprising acimixing a pharmaceutically acceptable carrier with a therapeutically effective amount of a disaccharide represented by formula (I) of claim 1.

12. A pharmaceutical composition useful for preventing or treating arthrosis, inflammatory diseases or blood clotting comprising a disaccharide represented by formula (I) of claim 1 and a pharmaceutically acceptable carrier.

13. A method for preventing or treating arthrosis comprising administering to a subject in need thereof, a therapeutically effective amount of a disaccharide represented by formula (I) of claim 1.

14. A method for preventing or treating inflammatory diseases comprising administering to a subject in need thereof, a therapeutically effective amount of a disaccharide represented by formula (I) of claim 1.

15. A method for preventing or treating blood clotting comprising administering to a subject in need thereof, a therapeutically effective amount of a disaccharide represented by formula (I) of claim 1.

* * * * *